US00PP16064P2

(12) United States Plant Patent
Jansen

(10) Patent No.: US PP16,064 P2
(45) Date of Patent: Oct. 25, 2005

(54) ***SILENE DIOICA* PLANT NAMED 'VALLEY HIGH'**

(50) Latin Name: *Silene dioica*
Varietal Denomination: Valley High

(75) Inventor: Robert D. Jansen, Beaverton, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 140 days.

(21) Appl. No.: 10/872,294

(22) Filed: Jun. 18, 2004

(51) Int. Cl.[7] ..... A01H 5/00
(52) U.S. Cl. ..... Plt./263
(58) Field of Search ..... Plt./263

*Primary Examiner*—Anne Marie Grunberg
*Assistant Examiner*—Annette H Para
(74) *Attorney, Agent, or Firm*—Klarquist Sparkman, LLP

(57) ABSTRACT

A new and distinct cultivar of *Silene dioica* plant given the cultivar name 'Valley High' characterized by creamy yellow leaves with irregular olive green centers and excellent vigor.

1 Drawing Sheet

Botanical classification: *Silene dioica.*
Variety denomination: 'Valley High'.

BACKGROUND OF THE INVENTION

The present invention relates to a new and distinct cultivar of a hardy perennial, *Silene dioica,* known by the cultivar name of 'Valley High'. The genus *Silene* is a member of the family Caryophyllaceae.

The new cultivar originated as a mutation from tissue culture of *Silene dioica* 'Jade Valley' (U.S. Plant Pat. No. 11,459).

SUMMARY OF THE INVENTION

This new cultivar is characterized by:

1) Creamy yellow leaves with a two-tone, grey green center.

2) Vigor.

Asexual propagation by tissue culture as done in Canby, Oreg., shows that the foregoing characteristics and distinctions come true to form and are established and transmitted through succeeding propagations. This new cultivar has been reproduced only by asexual propagation (cuttings and tissue culture). Each of the progeny exhibits identical characteristics to the original plant. The present invention has not been evaluated under all possible environmental conditions. The phenotype may vary with variations in environment without a change in the genotype of the plant.

BRIEF DESCRIPTION OF THE PHOTOGRAPH

The photograph shows a two-year-old plant grown in the ground in the garden in the spring in Canby, Oreg.

DETAILED PLANT DESCRIPTION

The following is a detailed description of the new cultivar based on observations of a two-year-old specimen grown in a one-gallon container in a greenhouse in Canby, Oreg. The color descriptions are all based on The Royal Horticultural Society Colour Chart.

Botanical classification: *Silene dioica.*
Variety denomination: 'Valley High'.

Plant:
- *Type.*—Herbaceous perennial.
- *Form.*—Low growing with spreading shoots and erect flowering stems.
- *Hardiness.*—USDA Zone 6 to 9.
- *Size.*—11 cm tall and 33 cm wide.
- *Habit.*—Clumping.

Stem:
- *Type.*—Decumbent.
- *Size.*—1 to 7 cm long, 5 mm wide.
- *Color.*—Light brown, Greyed Brown 199C to light green, Yellow Green 149D before leaf rosette.

Basal leaves:
- *Type.*—Simple, evergreen.
- *Arrangement.*—Rosette.
- *Shape.*—Oblanceolate.
- *Venation.*—Pinnate.
- *Margins.*—Entire, undulate.
- *Apex.*—Acute.
- *Base.*—Attenuate.
- *Blade size.*—3 to 9 cm long and 2 to5 cm wide.
- *Vestiture.*—Scabrous on topside.
- *Surface.*—Matte.
- *Texture.*—Rough.
- *Petiole length.*—3 to 9 cm.
- *Petiole color.*—Yellow Green 147B with Greyed Purple 187B at base.

Stem leaves:
- *Type.*—Simple, evergreen.
- *Arrangement.*—Opposite.
- *Shape.*—Oblanceolate to elliptic.
- *Venation.*—Pinnate.
- *Margins.*—Entire, slightly undulate.
- *Apex.*—Acute.
- *Base.*—Attenuate.
- *Blade size.*—3 to 7.5 cm long and 1.5 to 4 cm wide.
- *Vestiture.*—Scabrous on topside.
- *Surface.*—Matte.
- *Texture.*—Rough.
- *Petiole length.*—0 to 4 cm.

Petiole color: Yellow Green 147B with Greyed Purple 187B at base.

Leaf color:

*Topside.*—Creamy yellow, Greyed Yellow 160A with Yellow Green 147A to C in the middle in an irregular pinnate pattern. The new leaves are Yellow Green 145A with Green 138A to C in the middle.

*Bottom side.*—Yellow Green 151A with Yellow Green 147C in the middle.

Inflorescence:

*Type.*—Panicle-like cymes.

*Number of flowers.*—14 per flowering branch.

*Number of branches per stem.*—5.

*Number of flowering stems.*—80 on a three year old plant.

*Peduncle.*—With 5 to 9 petiolate cauline leaves, orbicular to ovate, blades 2 to 5 cm long and 1 to 7 cm wide with an incised and crenate margin. Height — 50 to 61 cm. Diameter — 0.5 cm near base. Color — Greyed Purple 187B to D to 183A. Vestiture — Glandular.

*Branching.*—2 to 3 times.

*Pedicel.*—None to very short.

*Bloom period.*—April to June in Canby, Oreg.

Flower bud:

*Size.*—12 to 13 mm deep and 3 mm wide where exerted from calyx.

*Description.*—Cylindrical.

*Color.*—Red Purple 73A.

Flower:

*Type.*—Imperfect, staminate, actionomorphic, polypetalous.

*Shape.*—Salverform.

*Size.*—18 mm deep tube and 20 mm wide where lobes flare.

*Corolla color.*—Red Purple 73A with a white eye and base, White 155D.

*Petal description.*—4 separate, base is 15 mm long and 3 mm wide, limb is heart shaped, two lobed, cut to ½ length, 9 mm wide and 10 mm deep.

*Calyx.*—Cylindrical, with long glandular hairs, with 5 teeth.

*Calyx size.*–14 mm deep and 4 mm wide.

*Calyx color.*—Greyed Purple 183C.

*Stamen number.*—10.

*Anther color.*—Cream, Yellow 4D.

*Pollen color.*—White 155D.

*Fragrance.*—None.

*Lastingness.*—Each flower cluster blooms for 3 to 4 weeks on the plant.

Fruit and seed: None produced as this is a male clone.

Pest and disease tolerance: Snails, slugs, whiteflies, mites, and aphids could be a problem in some areas. No disease problems like rust or smut have been observed.

Culture: Prefers moist, well drained soil in part sun.

COMPARISONS TO SIMILAR *SILENE DIOICA*

Compared to its parent, *Silene dioica* 'Jade Valley' (U.S. Plant Pat. No. 11,459), this new cultivar has longer, thicker leaves and a larger green center giving the plant good vigor. *Silene dioica* 'Jade Valley' was difficult to produce and grow due to its almost totally white leaves, which reduced its vigor.

Compared to *Silene dioica* 'Clifford Moor' (an unpatented plant), this new cultivar has darker pink flowers, larger, broader leaves with a cream rather than light green margin.

I claim:

1. A new and distinct cultivar of *Silene dioica* plant given the cultivar name 'Valley High' as illustrated and described characterized by creamy yellow leaves with irregular olive green centers and excellent vigor.

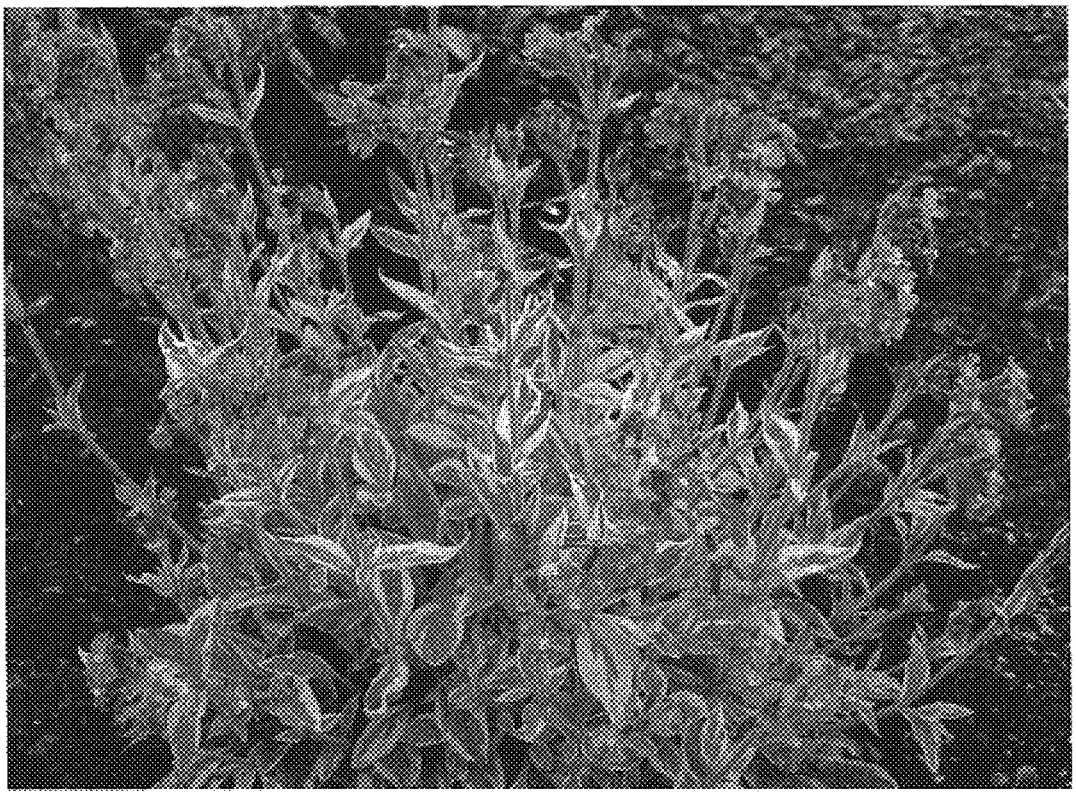

* * * * *